United States Patent
Moazzami et al.

(10) Patent No.: US 8,904,888 B2
(45) Date of Patent: Dec. 9, 2014

(54) DRINKING SIMULATOR

(75) Inventors: Saied Mostafa Moazzami, Loma Linda (IR); Berahman Sabzevari, Loma Linda (IR)

(73) Assignee: Mashhad University of Medical Sciences (MUMS), Mashhad (IR)

( * ) Notice: Subject to any disclaimer, the term of this patent is extended or adjusted under 35 U.S.C. 154(b) by 284 days.

(21) Appl. No.: 13/459,086

(22) Filed: Apr. 28, 2012

(65) Prior Publication Data

US 2013/0284284 A1    Oct. 31, 2013

(51) Int. Cl.
*F16K 49/00* (2006.01)

(52) U.S. Cl.
USPC ............................................. 73/865.6; 73/866

(58) Field of Classification Search
USPC .................................. 73/865.6, 866; 137/334
See application file for complete search history.

(56) References Cited

U.S. PATENT DOCUMENTS

| | | | | |
|---|---|---|---|---|
| 5,039,228 A | * | 8/1991 | Chalmers | 374/57 |
| 5,278,495 A | * | 1/1994 | Beaton et al. | 324/750.08 |
| 5,347,825 A | * | 9/1994 | Krist | 62/179 |
| 5,513,538 A | * | 5/1996 | Baker et al. | 73/865.6 |
| 6,213,636 B1 | * | 4/2001 | Chien | 374/57 |
| 6,722,154 B1 | * | 4/2004 | Tan et al. | 62/480 |
| 6,726,879 B2 | * | 4/2004 | Ng et al. | 422/417 |
| 7,249,530 B2 | * | 7/2007 | Agama et al. | 73/865.6 |
| 8,408,020 B2 | * | 4/2013 | Cole et al. | 62/259.2 |
| 8,485,039 B2 | * | 7/2013 | Provost et al. | 73/663 |
| 2009/0208357 A1 | * | 8/2009 | Garrett | 418/152 |
| 2011/0290328 A1 | * | 12/2011 | Jonsson | 137/1 |

* cited by examiner

*Primary Examiner* — John Fitzgerald
*Assistant Examiner* — Xin Zhong

(57) ABSTRACT

A drinking simulator provides for testing of dental samples under three different condition sets simultaneously. A first tank provides chilled liquid to testing chambers at a first temperature range, a second tank provides heated liquid to testing chambers at a second temperature range and a third tank provides heated liquid to testing chambers at a third temperature range. Shower heads in each of the tanks are provided to shower dental samples with the provided liquid. A human machine interface allows for user control of multiple showering modes and liquid temperatures and additionally displays testing conditions to the user.

15 Claims, 4 Drawing Sheets

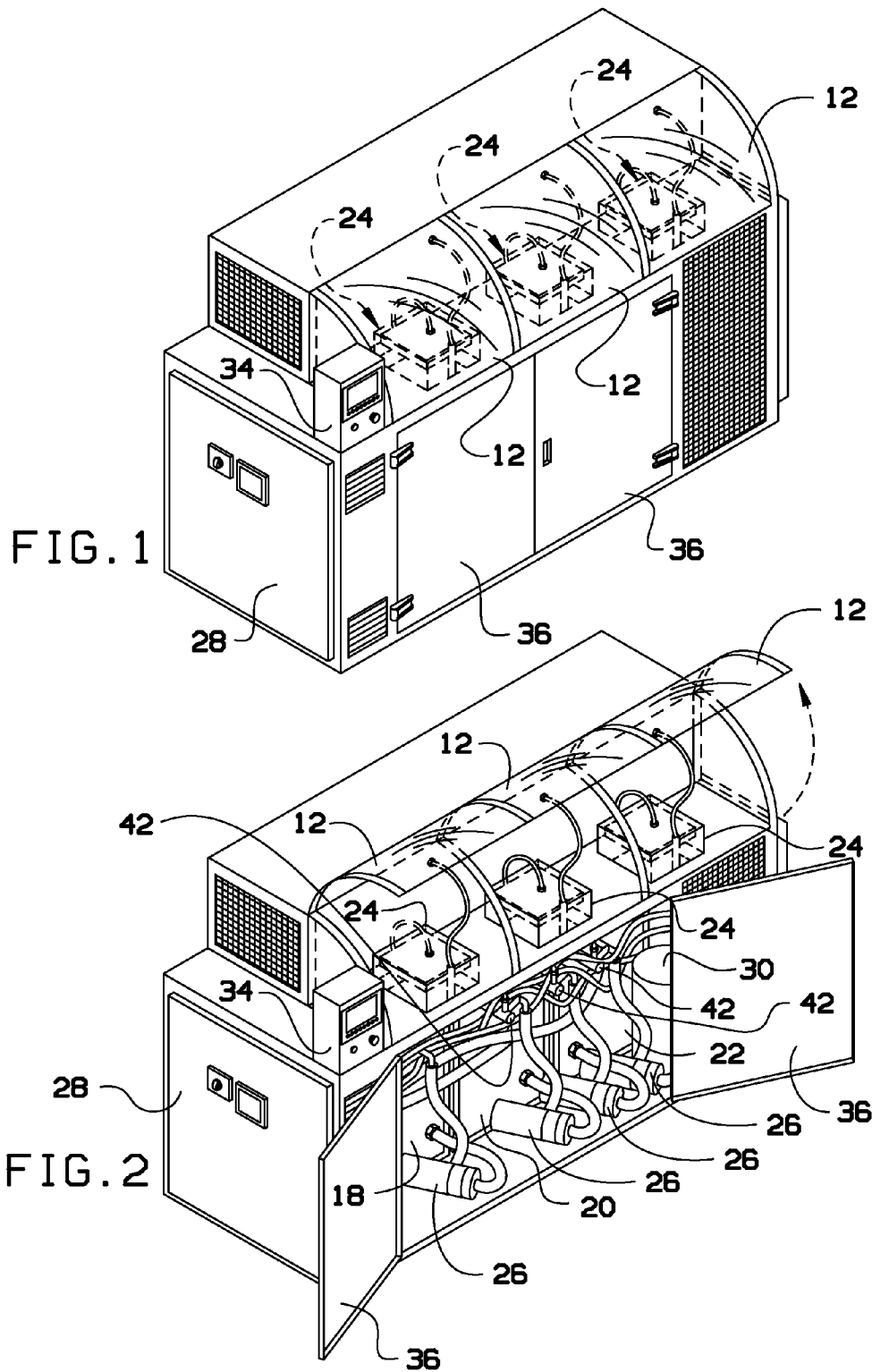

DRINKING SIMULATOR

BACKGROUND OF THE INVENTION

One of the important characteristic features of the oral cavity which has a great impact on the function of dental materials is the thermal change resulting from the consuming foods and drinks of different temperatures. Because the tooth and restoration materials have different thermal expansion coefficients, cold and hot drinks or foods exert different degrees of contraction and expansion in the tooth and dental filling materials. Eventually, this results in tiny gaps between them. By more accurately simulating oral conditions while studying dental materials and tooth structure, greater reliability in the results and greater certainty in applying these results to clinical conditions will be possible.

To simulate thermal shocks, studies typically use a thermal cycling unit. The common method of thermal cycling provides two liquid environments of 5° C. and 55° C. into which samples are placed in rapid succession. Despite its popularity in dental research, this method fails to accurately simulate the natural oral environment under in vitro conditions.

After a sip of hot tea or cold drink, the teeth and dental materials come into contact with the passing or showering liquid and then the saliva and normal oral temperatures surrounds them again. The balance temperature allows the stress exerted as a result of drinking liquids of different temperatures to be released without being accumulated in the material. This prevents the material from getting fatigued and broken very soon. However, this may not happen as a result of placing the samples in two different thermal baths of 5° C. and 55° C. in rapid and sudden succession since there is no balance temperature.

In conducting laboratory research, the materials, techniques and dental structure should be tested by the same shocks they receive in the oral cavity. The shocks can be exerted because of the temperature, chewing pressure, special eating or drinking habits, chemical elements such as acidic, basic, alcoholic, non-alcoholic and carbonated drinks as well as colored substances such as tea, coffee and juices. Research will allow for development of dental materials and techniques should be produced and developed so that they can resist such shocks.

SUMMARY OF THE INVENTION

The primary objective of the present invention is to provide a system for simulating drinking in a new generation of thermal cycling unit (chemical, color and thermal cycling unit). The present invention is capable of more accurately simulating the oral environment in terms of drinking behavior and balancing temperature in a way that can be used for experimental testing on dental structure, materials and techniques.

Secondary objectives of the present invention are to more accurately simulate, not only the thermal conditions, but also color and chemical conditions in the natural oral cavity in lab conditions. This provides the chance for the researchers to examine the effects of different colored drinks with different pH values.

Among the characteristic features of the invention, one can refer to the more similar and accurate simulation of thermal cycling of the oral environment, creating a balance temperature of 37° C. between two thermal shock, simulating the frequency and continuity of the drinking behavior, ability to exert chemical and color shocks by acidic, basic and other available drinks such as dairy-based and carbonated and non carbonated drinks; tea, coffee and other brewing drinks; sherbets and other fruit juices as well as alcoholic and non-alcoholic drinks in different cultures in lab environment.

The invented system generally has two parts: the hardware and the software parts. The hardware consists of the mechanical and electronic parts including liquid storage tanks, immersion and showering or testing chambers, heating and cooling systems, electric panel, corrosion-resistant pumps, electric valves, water treatment system, PLC (Programmable Logical Controller) and HMI (Human Machine Interface).

The system consists of three tanks containing a liquid (water or other drinking or testing liquids) whose temperature can be changed by heating or cooling units installed around each tank.

The system is also equipped with three testing or showering chambers instead of one in order to improve the simulation performance in different laboratory experiments conducted simultaneously.

An integrated software application is responsible for controlling heating and cooling systems, electric valves, pumps, automatic filling systems of tanks as well as the sensors. Furthermore, the software application communicates the data of the liquid conduits, tank temperature and other functions to human machine interface (HMI). This part also includes the software codes as well as the application programs required for controlling the mechanical and electronic sections of the system.

For each showering chamber, the controlling software decides which liquid, from which tank, at what temperature, for how long, with what sequence and pattern is to be showered which is similar to drinking behavior.

This unique drinking simulator performs chemical, color, and thermal cycling to closely simulate oral conditions in laboratory testing of dental materials, techniques and structures.

BRIEF DESCRIPTION OF THE DRAWINGS

FIG. 1 illustrates a front perspective view of the drinking simulator of the present invention.

FIG. 2 illustrates internal components of the present invention from a front perspective view.

DETAILED DESCRIPTION OF THE INVENTION

Figure 3:
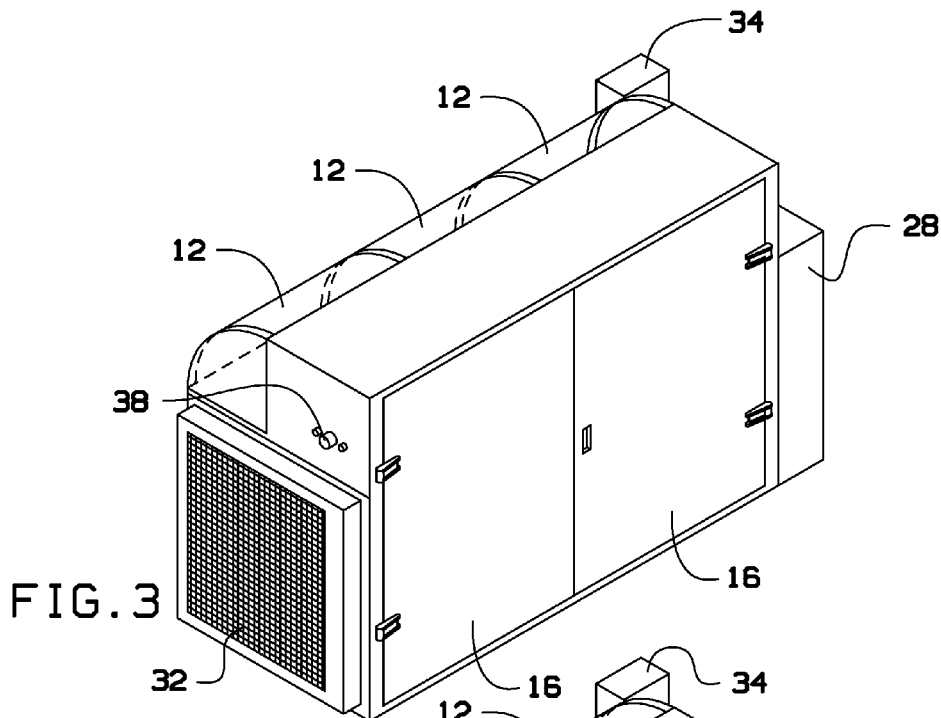
FIG. 3 illustrates a rear perspective view of the invention.
Figure 4:
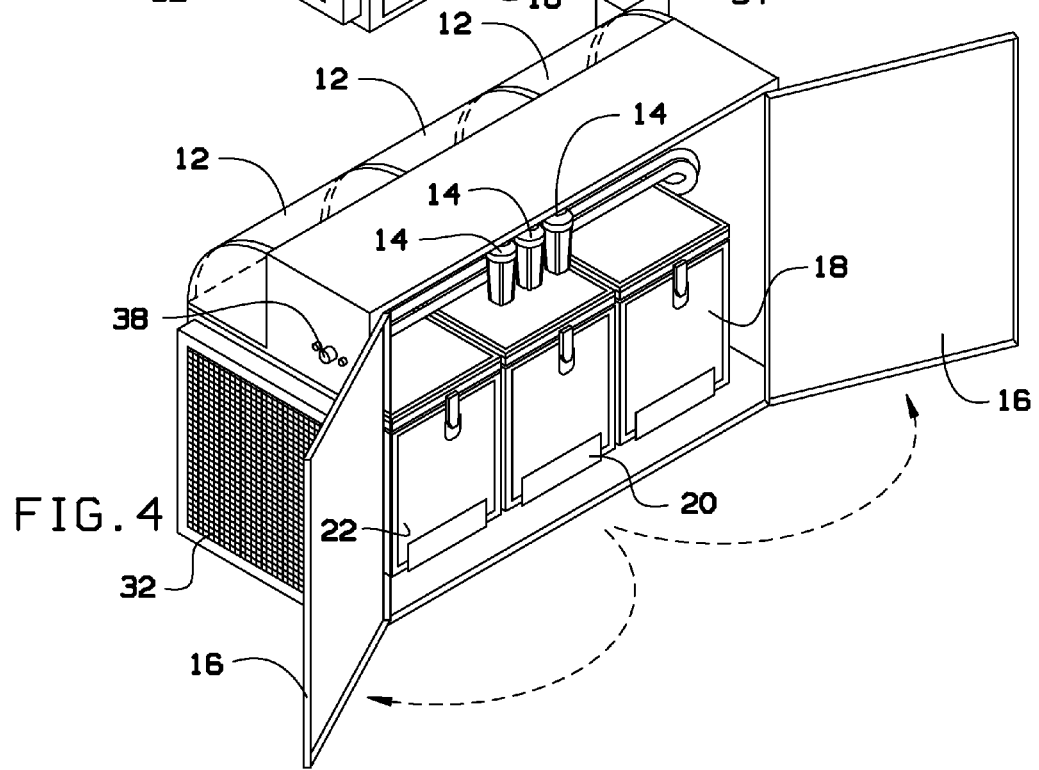
FIG. 4 illustrates internal components of the present invention from a rear perspective view.
Figure 5:
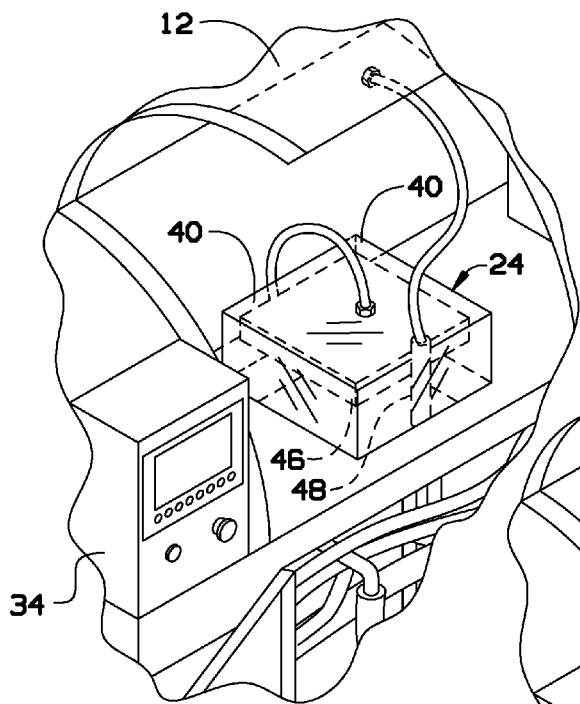
FIG. 5 illustrates a detail perspective view of the present invention with closed showering chamber.
Figure 6:
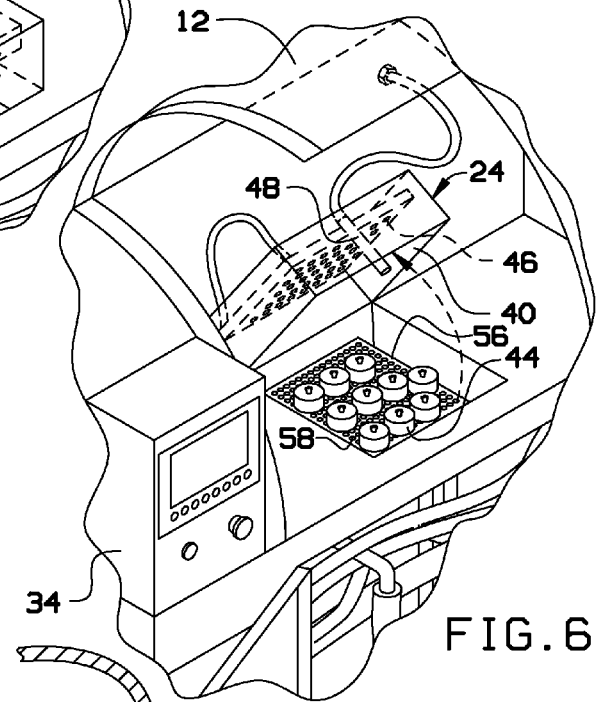
FIG. 6 illustrates a detail perspective view of the present invention with open showering chamber.
Figure 7:
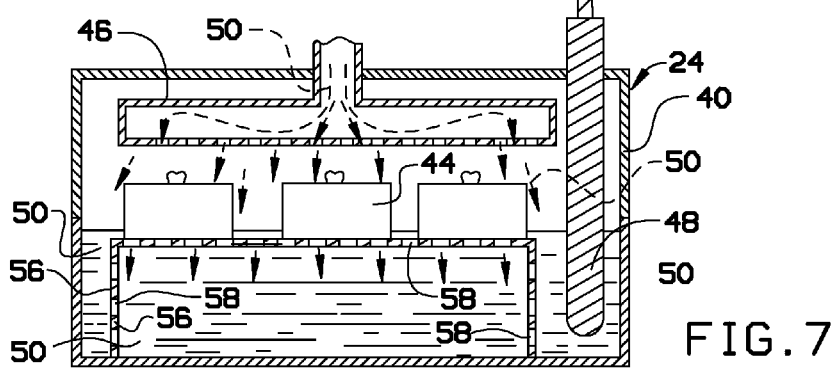
FIG. 7 illustrates a section detail view of the showering chamber.
Figure 8:
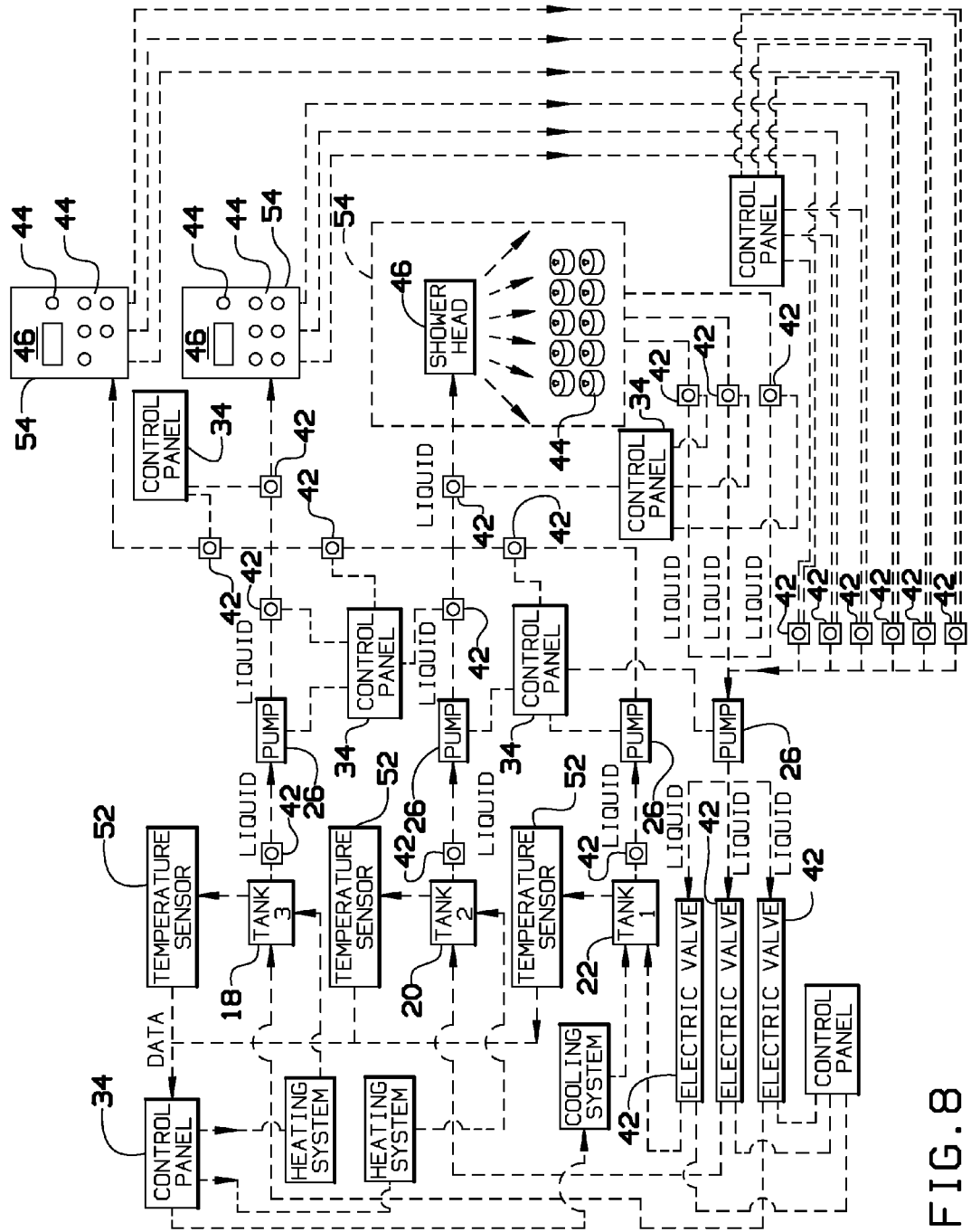
FIG. 8 illustrates a component schematic view of the present invention.

As mentioned above, the system of the present invention generally has both hardware and software components which will be described with reference to FIGS. 1-8.

The hardware consists of the mechanical and electronic parts including liquid storage tanks, immersion and showering or testing chambers, heating and cooling systems, electric panel, corrosion-resistant pumps, electric valves, water treatment system, PLC (Programmable Logical Controller) and HMI (Human Machine Interface).

The overall hardware of the present invention is of the general form of a cabinet having approximate dimensions 140×200×90 cm, an exterior and an interior. The exterior includes a plurality of front doors 36 and a plurality of rear doors 16 through which a user may access the interior of the simulator and, thereby, liquid storage tanks, pumps and electric valves.

All three of the liquid storage tanks 18, 20 and 22 are equipped with thermal sensors such as thermometers 52. Liquids are preferably maintained in tanks 18, 20 and 22 at 5, 37 and 55 degrees Celsius respectively. However, a wide range of thermal conditions are possible.

A first tank 18 within said interior of said simulator and in fluid communication with the showering heads to deliver liquid to the showering testing chambers. Tank 18 is equipped with a cooling system in order to maintain liquids at temperatures between 0 and 10 degrees Celsius. The cooling system includes a chilling unit, a condenser 30, a condenser fan and a compressor. The cooling system has SS304 coils which are resistant to corrosion and the condenser fan is contained behind a condenser fan protective mesh 32.

A second tank 20 within said interior of said simulator and in fluid communication with said showering heads to deliver liquid to showering testing chambers. Tank 20 is equipped with a heating system for providing liquids at temperatures between 32 and 42 degrees Celsius. The heating system includes heating coils resistant to corrosion.

A third tank 22 within said interior of said simulator and in fluid communication with the showering heads to deliver liquid to the showering testing chambers. Tank 22 is equipped with a heating system for providing liquids at temperatures between 50 and 60 degrees Celsius. The heating system includes heating coils resistant to corrosion.

The three tanks 18, 20 and 22 supply water at the desired temperatures to three showering or testing chambers 54 of the system. Chambers 54 are used for showering liquid 50 on dental samples 44 imitating the flow of liquids moving past the teeth or immersing the samples in the liquid. The showering testing chambers each having exterior lids 12 and interior lids 24, and include a liquid level sensor 48 and a sample support member 56 for supporting dental samples 44. Sample support table includes a plurality of perforations 58.

Showering of liquid 50 in the showering and immersing or testing chambers 54 is accomplished by square shower heads 46 capable of either continuous or pulse mode. The functions are controlled by liquid level sensors 48 in chambers 54 and electric valves 42 and pumps 26 at the base of the system. The square showering heads 46 are connected to respective showering testing chamber interior lids 24 and capable of delivering.

Liquids are circulated through conduits and pumped to the three showering or testing chambers 54 by way of four corrosion-resistant pumps 26 provided with magnetic clutch and automatic disconnector. Pumps 26 are preferably Teflon-coated and may also pump the liquid 50 to external lab systems as artificial.

A first corrosion resistant pump provides for pumping liquid from the first tank to the showering heads, a second corrosion resistant pump provides for pumping liquid from the second tank to the showering heads and a third corrosion resistant pump provides for pumping liquid from the third tank to the showering heads. A fourth corrosion resistant pump provides for pumping liquid from the showering testing chambers to the tanks.

Twenty two electric valves 42 to control the flow of liquid 50 to and from the storage tanks 18, 20 and 22 to the showering and immersion chambers 54. The conduits and connecting parts of the system as well as the one-way valves are corrosion-resistant and insulated. Nine electric valves control liquid flow between the showering testing chambers and the fourth pump, ten electric valves control liquid flow between the tanks and the square showering heads and three electric valves control liquid flow between the fourth pump and the tanks.

The system is also equipped a liquid tap connection 38 for connecting the drinking simulator 10 to a liquid source. Water treatment filters 14 can be directly attached to the liquid tap connection 38 to provide refill to tanks 18, 20 and 22 automatically. Manual refilling the tanks with other testing liquids is also possible.

All operations of the drinking simulator system 10 of the present invention are controlled by a Programmable Logic Controller (PLC) upon which software is installed. The PLC system is used for control of the operation of the system including tanks, testing chambers, conduits, pumps and electric valves. Residual Recurrent Device, adaptors and other electronic controlling units make up the PLC. Through the PLC simulator system also provides the operator with an opportunity to choose a wide range of programs and to change thermal cycling programs, if necessary.

To show different operations in progress (control panel), the new system has been equipped with a color, touch-controlled Human Machine Interface (HMI) 34 which also allows the operator to make any required adjustments. It is possible to program the sequence and time of showering liquids on the samples in different chambers. Parts of the software system and program codes of the system are controlled through this interface. In case of any mechanical failure, the audio-visual alarming system warns the operators. The alarm system can make the whole machine stop working. Another part of the software system and program codes of the system are controlled through this interface.

In some embodiments the control panel includes a display for presenting information pertaining to said liquid level sensors 48 and said thermometers 52 and an input component permitting the user to make inputs to the control panel affecting the heating mechanisms to adjust the temperature of one of the second and third tanks, the cooling mechanisms to adjust the temperature of said first tank, a pumping condition of said pumps, and an open or close condition of said electric valves In addition to offering some default options for thermal cycling, the software system of the machine enables the operators to regulate and change the variables in the thermal cycling at will. These changes can include the number, the sequence and time of the cycles as well as choosing the showering or immersion modes, and the tanks and the chambers involved in cycling and the temperature of each chamber.

The software system installed between the PLC and the HMI 34 is programmed to have default options for exerting thermal cycles. The defaults include the following factors: immersion (old model) or showering pattern (new model which simulates the drinking behavior and allows the liquid to flow over the samples), pulse or continuous modes of showering which imitates the frequent or the non-stop modes of drinking, time for each cycle, number of all cycles. Like previous models, the system allows the samples to be immersed in the liquid in the showering chambers. The software also enables the operator to choose and adjust the specific features of the cycle. The controlling software system provides a chance for the operator to control which liquid, from which tank, at what temperature, for how long, with which sequence and pattern should be showered on the samples in each chamber.

The software is responsible for controlling the heating and cooling systems, electric valves, the pumps, automatic filling systems of tanks as well as the sensors of the machine. In addition, this part communicates the data of the liquid conduits, tank temperature and other functions to HMI 34. This part also includes the software codes as well as the application programs required for controlling the mechanical and electronic sections of the system.

The simulation system enables examining the effects of thermal, chemical and color cycling with or without loading cycle on dental structures, materials and products in dental laboratory researches in different fields of dentistry (operative, dental materials, prosthesis, orthodontics, pediatric dentistry and implants). The invented system has greatly improved and validate the results of dental researches with more simulation capability.

Different forms of thermal cycling, Different forms of chemical cycling, different forms of color cycling, Different Combined Shocks are possible. The system can be attached to other lab equipment such as load cycler and artificial toothbrush units. It can also exert thermal, chemical, color and mechanical shocks simultaneously. The simulator system has the ability to use different closed systems of chemical cycles in examining the chemical durability of dental materials and tooth structure. Exploring effects of different detergent, bleaching and disinfecting substances on medical and dental equipment; disinfecting the equipments and extracted teeth.

The present invention can be connected to other lab equipment such as artificial tooth brushes and load cycler to perform load, thermal, color and chemical cycling simultaneously which enables four operators to work with different thermal cycling programs at the same time using three showering chambers 54 as well as other attached additional equipment.

Outside of the dental field, the present invention is anticipated as facilitating the examination of effects of different detergent, bleaching and disinfecting substances on clothing, surfaces and cutlery and crockery or the examination of the effects of acidic rain on different external covers of the buildings.

While the invention has been described with respect to certain specific embodiments, it will be appreciated that many modifications and changes may be made by those skilled in the art without departing from the spirit of the invention. It is intended, therefore, by the appended claims to cover all such modifications and changes as fall within the true spirit and scope of the invention.

We claim:

1. A drinking simulator in the general form of a cabinet comprising:
    an exterior;
    an interior;
    first, second and third showering testing chambers each having exterior lids and interior lids, and containing a liquid level sensor and a sample support table including perforations;
    first, second and third square showering heads connected to respective first, second and third showering testing chambers interior lids and capable of delivering liquid, in both continuous and pulse modes, to dental samples held in said first, second and third showering testing chambers;
    a first tank within said interior of said simulator and in fluid communication with said showering heads to deliver liquid to said showering testing chambers, said first tank including a cooling mechanism and a first thermometer such that liquid held by said first tank for delivery to said showering heads may be maintained at a desired temperature of between approximately 0 and approximately 10 degrees Celsius;
    wherein said cooling mechanism including a condenser and a condenser fan;
    a second tank within said interior of said simulator and in fluid communication with said showering heads to deliver liquid to said showering testing chambers, said second tank including a first heating mechanism and a second thermometer such that liquid held by said second tank for delivery to said showering heads may be maintained at a desired temperature of between approximately 32 and approximately 42 degrees Celsius;
    a third tank within said interior of said simulator and in fluid communication with said showering heads to deliver liquid to said showering testing chambers, said third tank including a second heating mechanism and a third thermometer such that liquid held by said third tank for delivery to said showering heads may be maintained at a desired temperature of between approximately 50 and approximately 60 degrees Celsius;
    wherein said heating mechanisms include corrosion resistant heating coils;
    a first corrosion resistant pump for pumping liquid from said first tank to said showering heads;
    a second corrosion resistant pump for pumping liquid from said second tank to said showering heads;
    a third corrosion resistant pump for pumping liquid from said third tank to said showering heads;
    a fourth corrosion resistant pump for pumping liquid from said first, second and third showering testing chambers to said first, second and third tanks;
    wherein each of said corrosion resistant pumps are equipped with a magnetic clutch and an automatic disconnector;
    nine electric valves for controlling liquid flow between said first second and third showering testing chambers and said fourth pump;
    ten electric valves for controlling liquid flow between said first, second and third tanks and said first second and third square showering heads;
    three electric valves for controlling liquid flow between said fourth pump and said first, second and third tanks;
    wherein said exterior includes a plurality of front doors and a plurality of rear doors through which a user may access the interior of the simulator and, thereby, said first, second and third tanks, as well as said pumps and said electric valves;
    a control panel including:
        a display for presenting information pertaining to said liquid level sensors and said thermometers;
        an input component permitting the user to make inputs to said control panel affecting:
            the cooling mechanism to adjust the temperature of said first tank,
            the heating mechanisms to adjust the temperature of one of said second and third tanks,
            a pumping condition of said pumps, and
            an open or close condition of said electric valves;
    a liquid tap connection for connecting the drinking simulator to a liquid source; and
    a liquid treatment filter for filtering liquid from said water source into said first, second and third tanks.

2. The drinking simulator of claim 1, wherein:
    said interior lids are transparent.

3. A drinking simulator in the general form of a cabinet comprising:
    an exterior;
    an interior;

a plurality of showering testing chambers each having exterior and interior lids, and containing a liquid level sensor and a sample support table including perforations;

a plurality of showering heads connected to said interior lids and capable of delivering liquid, in both continuous and pulse modes, to dental samples held in said showering testing chambers;

a plurality of warm tanks within said interior of said simulator and in fluid communication one or more of said showering heads to deliver liquid to said showering testing chambers, said plurality of warm tanks including a plurality of heating mechanisms and a plurality of thermometers such that liquid held said tanks for delivery to said one or more showering heads may be maintained at a desired temperature;

wherein said heating mechanisms include corrosion resistant heating coils;

at least one cold tank within said interior of said simulator and in fluid communication with at least one of said showering heads to deliver liquid to at least one of said showering testing chambers, said cold tank including a cooling mechanism and at least one thermometer such that liquid held by said at least one cold tank for delivery to said at least one of said showering testing chambers may be maintained at a desired temperature below that of said warm tanks;

wherein said cooling mechanism including a condenser and a condenser fan;

a plurality of corrosion resistant pumps for pumping liquid from said warm tanks and said at least one cold tank to said plurality of showering heads and from said showering testing chambers to said warm tanks and said at least one cold tank;

wherein each of said corrosion resistant pumps are equipped with a magnetic clutch and an automatic disconnector;

a plurality of electric valves for controlling liquid flow between said showering testing chambers, said warm tanks, said at least one cold tank and said pumps;

wherein said exterior includes a plurality of front doors and a plurality of rear doors through which a user may access the interior of the simulator and, thereby, said tanks, said pumps and said electric valves;

a liquid tap connection for connecting the drinking simulator to a liquid source;

a liquid treatment filter for filtering liquid from said liquid source into said warm tanks and said cold tanks; and a control panel including:
  a display for presenting information pertaining to said liquid level sensors and said thermometers;
  an input component permitting the user to make inputs to said control panel affecting:
    the heating mechanisms to adjust the temperature of said first warm tanks,
    the cooling mechanism to adjust the temperature of said at least one cold tank,
    a pumping condition of said pumps, and
    an open or close condition of said electric valves.

4. The drinking simulator of claim 3, wherein:
said interior lids are transparent.

5. A drinking simulator to simulate the oral environment during specific drinking behaviors comprising:
an exterior;
an interior;
a plurality of showering testing chambers;
a plurality of showering heads;
a plurality of warm tanks within said interior of said simulator and in fluid communication one or more of said showering heads to deliver liquid to said showering testing chambers;

at least one cold tank within said interior of said simulator and in fluid communication with at least one of said showering heads to deliver liquid to said at least one of said showering testing chambers;

a plurality of corrosion resistant pumps for pumping liquid from said warm tanks and said at least one cold tank to said plurality of showering heads and from said showering testing chambers to said warm tanks and said at least one cold tank;

a plurality of electric valves for controlling liquid flow between said showering testing chambers, said warm tanks, said at least one cold tank and said pumps;

a control panel;

a liquid tap connection for connecting the drinking simulator to a liquid source; and a liquid treatment filter for filtering liquid from said liquid source into said warm tanks and said cold tank.

6. The drinking simulator set forth in claim 5, wherein:
said showering testing chambers each have exterior lids and interior lids, and
contain a liquid level sensor and a sample support table.

7. The drinking simulator set forth in claim 6, further comprising:
a plurality of perforations in said sample support table.

8. The drinking simulator set forth in claim 6, wherein:
said plurality of showering heads are connected to said interior lids and capable of delivering liquid, in both continuous and pulse modes, to dental samples held in said showering testing chambers.

9. The drinking simulator set forth in claim 5, wherein:
said plurality of warm tanks comprise a plurality of heating mechanisms and a plurality of thermometers such that liquid held said tanks for delivery to said showering heads may be maintained at a desired temperature.

10. The drinking simulator set forth in claim 9, wherein:
said heating mechanisms include corrosion resistant heating coils.

11. The drinking simulator set forth in claim 5, wherein:
said at least one cold tank comprises a cooling mechanism and at least one thermometer such that liquid held by said at least one cold tank for delivery to said at least one of said showering testing chambers may be maintained at a desired temperature below that of said warm tanks.

12. The drinking simulator set forth in claim 11, wherein:
said cooling mechanism including a condenser and a condenser fan.

13. The drinking simulator set forth in claim 5, wherein:
wherein each of said corrosion resistant pumps are equipped with a magnetic clutch and an automatic disconnector.

14. The drinking simulator set forth in claim 5, wherein:
said exterior includes a plurality of front doors and a plurality of rear doors through which a user may access the interior of the simulator and, thereby, said tanks, said pumps and said electric valves.

15. The drinking simulator set forth in claim 5, wherein:
said control panel comprises a display for presenting information pertaining to said liquid level sensors and said thermometers; and
an input component permitting the user to make inputs to said control panel affecting:
  the heating mechanisms to adjust the temperature of said second and third warm tanks, the cooling mechanism to adjust the temperature of said
   at least one cold tank,
a pumping condition of said pumps, and
an open or close condition of said electric valves.

\* \* \* \* \*